(12) United States Patent
Israelson et al.

(10) Patent No.: US 9,622,903 B2
(45) Date of Patent: Apr. 18, 2017

(54) OSTOMY APPLIANCE

(75) Inventors: Dorrit Diana Israelson, Gentofte (DK); Hasse Buus, Humlebaek (DK); Charlotte Klein, Broenshoej (DK); Kristoffer Hansen, Maaloev (DK); Henrik Edvardsen, Copenhagen N (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 14/127,501

(22) PCT Filed: Jun. 29, 2012

(86) PCT No.: PCT/DK2012/050237
§ 371 (c)(1),
(2), (4) Date: Dec. 19, 2013

(87) PCT Pub. No.: WO2013/000482
PCT Pub. Date: Jan. 3, 2013

(65) Prior Publication Data
US 2014/0114265 A1    Apr. 24, 2014

(30) Foreign Application Priority Data

Jun. 30, 2011   (DK) ................................ 2011 70346

(51) Int. Cl.
*A61F 5/443* (2006.01)
*A61F 5/448* (2006.01)
(Continued)

(52) U.S. Cl.
CPC .............. *A61F 5/443* (2013.01); *A61F 5/448* (2013.01); *A61F 13/15211* (2013.01);
(Continued)

(58) Field of Classification Search
USPC .......................................................... 604/342
See application file for complete search history.

(56) References Cited

U.S. PATENT DOCUMENTS

| 4,681,574 A | 7/1987 | Eastman |
| 4,762,738 A * | 8/1988 | Keyes ..................... A61F 5/445 |
| | | 428/34.3 |

(Continued)

FOREIGN PATENT DOCUMENTS

| EP | 1101463 A1 * | 5/2001 | ............. A61F 5/448 |
| GB | 2311467 A1 | 10/1997 | |

(Continued)

*Primary Examiner* — Tatyana Zalukaeva
*Assistant Examiner* — Guy K Townsend
(74) *Attorney, Agent, or Firm* — Coloplast Corp., Coloplast A/S; Nick Baumann

(57) ABSTRACT

An ostomy appliance for attachment to a stoma, the ostomy appliance comprising: an adhesive wafer (100) defining a passage for receiving a stoma of a user, the adhesive wafer comprising a backing layer and a skin facing adhesive layer; and a collecting bag (116) which in use is secured to the adhesive wafer; wherein the adhesive wafer in a first adhesive zone has a first set of properties and in a second adhesive zone (104) has a second set of properties, the first zone defining three or more radially extending zones, wherein the second zone defines one or more interconnecting parts (110), each of which interconnects at least two of the radially extending zones (108).

23 Claims, 2 Drawing Sheets

(51) Int. Cl.
*A61F 13/15* (2006.01)
*A61F 5/449* (2006.01)

(52) U.S. Cl.
CPC ..... *A61F 2005/4495* (2013.01); *Y10T 428/24* (2015.01); *Y10T 428/24273* (2015.01)

(56) References Cited

U.S. PATENT DOCUMENTS

| | | | | |
|---|---|---|---|---|
| 4,804,377 | A * | 2/1989 | Hanifl | A61F 5/443 4/144.2 |
| 6,602,232 | B1 * | 8/2003 | Keyes | A61F 5/448 604/338 |
| 2003/0060786 | A1 * | 3/2003 | Olsen | A61F 5/448 604/342 |
| 2003/0093042 | A1 * | 5/2003 | Leisner | A61F 5/448 604/337 |
| 2006/0195053 | A1 * | 8/2006 | Oelund | A61F 5/443 602/43 |
| 2009/0234313 | A1 | 9/2009 | Mullejeans et al. | |
| 2009/0312685 | A1 * | 12/2009 | Olsen | A61F 5/443 602/54 |
| 2010/0114044 | A1 * | 5/2010 | Cramer | A61F 5/448 604/332 |
| 2010/0198176 | A1 * | 8/2010 | Stroebech | A61F 5/443 604/344 |
| 2010/0204665 | A1 * | 8/2010 | Stroebech | A61F 5/443 604/344 |
| 2010/0217215 | A1 | 8/2010 | Lykke et al. | |
| 2011/0213321 | A1 * | 9/2011 | Fattman | A61F 5/448 604/344 |
| 2012/0123363 | A1 * | 5/2012 | Grum-Schwensen | A61F 5/448 604/342 |
| 2012/0143155 | A1 * | 6/2012 | Edvardsen | A61F 5/4404 604/318 |
| 2014/0114265 | A1 * | 4/2014 | Israelson | A61F 5/443 604/342 |
| 2014/0128826 | A1 * | 5/2014 | Klein | A61F 5/443 604/344 |

FOREIGN PATENT DOCUMENTS

| | | |
|---|---|---|
| GB | 2473667 A1 | 3/2011 |
| RU | 2008151158 A | 6/2010 |
| WO | 0185074 A1 | 11/2001 |
| WO | 2004087004 A2 | 10/2004 |

\* cited by examiner

OSTOMY APPLIANCE

FIELD OF THE INVENTION

The present invention relates to an ostomy appliance comprising an adhesive wafer defining a first and a second zone. The first zone defines three or more radially extending zones, at least two of which are interconnected by interconnecting parts.

BACKGROUND OF THE INVENTION

Ostomy appliances with non-rounded adhesive wafers have the disadvantage that each of radially extending parts of the adhesive wafer must be detached separately in order to remove the entire adhesive wafer. This causes removal of such adhesive wafers to be time consuming and cumbersome.

It is an object of one or more embodiments of the present invention to provide an ostomy appliance which overcomes this problem.

DESCRIPTION OF THE INVENTION

In a first aspect, the present invention relates to an ostomy appliance for attachment to a stoma, the ostomy appliance comprising:

an adhesive wafer defining a passage for receiving a stoma of a user, the adhesive wafer comprising a backing layer and a skin facing adhesive layer; and a collecting bag which in use is secured to the adhesive wafer;

wherein the adhesive wafer in a first adhesive zone has a first set of properties and in a second adhesive zone has a second set of properties, the first zone defines a center zone from which three or more radially extending zones extend towards the rim of the wafer, the second zone defines one or more interconnecting parts, each of which interconnects at least two of the radially extending zones of the first zone, wherein a part of the second zone defines at least 30% of the total circumference of the outer rim of the adhesive wafer.

One advantage of the present invention is that two neighboring radially extending zones which are interconnected by an interconnecting part may be removed in one and the same motion. The reason for this being that detachment of one of the two radially extending zones will cause the interconnecting part to be detached and thus also the other of the two radially extending zones. Thus, the wafer of the invention is able to provide a better fit to curved body surfaces due to the presence of the radially extending portions, such as a protruding stoma, but is at the same time easy to detach from the skin after use.

Moreover, the provision of an adhesive on the interconnecting part causes the interconnecting part to serve as a barrier between the ostomy and the surroundings. If no interconnecting part was provided between two neighboring radially extending zones, then it might be possible for fecal matter to escape in the space defined between these two radially extending zones.

Compared to a traditional adhesive wafer which is round or rounded (e.g. circular or oval), the provision of a combination of radially extending zones and interconnecting parts provides for an adhesive wafer which may be easier to attach to the skin of the user. As an example, the radially extending zones may have a first property while the interconnecting parts may have another property, such as being more flexible. Thus, it may be easier for the user to customize the adhesive wafer to the 3D-geometry of the peristomal area, such as in cases where the stoma is associated with a hernia. Preferably, the radially extending zones will together with the interconnecting parts provide a wafer having a substantially round outline. By substantially round outline is herein meant that the outline is circular or oval, not necessarily strictly symmetrical, but is having a pronounced rounded shape without distinct deviations. However, the wafer, a non-adhesive tab member, may be present at the rim of the wafer in order to ease initial grip during detachment of the wafer.

The collecting bag may be suitable for collecting waste material from the intestinal system of a human being. Accordingly, the ostomy appliance may be adapted for use in connection with colostomies, ileostomies or urostomies, both temporary and permanent types. However, the appliance may also be used for collecting fecal matter from the rectum of a person suffering from fecal incontinence without having undergone stoma surgery.

The passage defined in the adhesive wafer, may be circular, oval or polygonal in shape. It will be appreciated that in some embodiments, this passage is small enough to allow the user to customize the passage to the shape of the stoma of the user, while at the same time being large enough to allow a cutting means such as a scissor, to be inserted into the passage. Thus, in one embodiment, the largest dimension of the passage is below 50 mm, such as below 40 mm, such as below 30 mm, such as below 20 mm, such as below 15 mm, such as below 10 mm, such as below 5 mm.

The skin facing adhesive layer may comprise any suitable adhesive. The skin facing adhesive layer comprises a first skin-facing layer of the first zone and a second skin-facing layer of the second zone. The first and the second skin-facing adhesive layer zone may comprise the same adhesive or they may comprise different adhesives. The adhesive may comprise absorbent particles such as hydrocolloids.

The first zone may comprise a hydrocolloid adhesive and the second zone may comprise a substantially non-absorbing soft adhesive.

Preferred adhesives are soft adhesives, such as silicone or polyurethane adhesives. In one embodiment, the adhesive comprises a polyalkyleneoxide polymer and organosiloxane based cross-linked adhesive system. Other suitable adhesives may be styrene isoprene styrene block copolymer (SIS) or ethylene vinyl acetate (EVA) based adhesives.

In one embodiment, the backing layer comprises a polymer film, coating, laminate, textile or non-woven. The backing layer is preferably a highly flexible film, being strong enough for attachment of e.g. couplings and/or pouch and for removing the device in one piece, but soft enough to follow the movements of the body.

A preferred backing layer is a polyurethane film. Other suitable films may be polyurethane/polyolefin blends or laminates.

Preferably, the backing layer has thermoplastic elements that enable welding of e.g. a pouch or coupling ring to the adhesive wafer. Preferred thickness of the backing layer is between 15-100 μm, such as 15-60 μm, such as 30-60 μm in order to maintain the softness of the adhesive wafer.

During use, the collecting bag is secured to the adhesive wafer. Thus in one embodiment, the ostomy appliance is a one-piece ostomy appliance in which the collecting bag is permanently secured to the adhesive wafer, for example by adhesive or welding. In the latter embodiment, the collecting bag may be integrated with the wafer. The collecting bag may be secured to the adhesive wafer by means of an adhesive provided between the collecting bag and the adhesive wafer. The latter adhesive may be provided on the opposite side of the adhesive wafer than the skin facing adhesive layer. Alternatively, or as a supplement, the collecting bag may be coupled to the adhesive wafer by means of a mechanical coupling means.

In another embodiment, the collecting bag and the adhesive form a two-piece ostomy appliance which is delivered to the user in two pieces that must be connected to each other by the user. In the latter embodiment, the adhesive may be provided on mating surfaces of the collecting bag and the wafer. In one embodiment, the collecting bag is detachably attached to the adhesive wafer, i.e. such that the collecting bag may be detached from the adhesive wafer.

In one embodiment, the collecting bag is reattachably attached to the adhesive wafer. By reattachably attached shall be understood that the collecting bag is attached or attachable to the adhesive wafer such that it may subsequently be detached and reattached to the adhesive wafer.

In one embodiment, the shape of the adhesive wafer is round such as circular or oval. The skin facing adhesive layer may be covered by a release liner. The release liner may be siliconised or otherwise provided with a non-stick surface on the side which faces the skin facing adhesive layer. This release must be removed in order for the user to adhere the skin facing adhesive layer to the skin of the user and does not form a part of the invention.

The first zone may define a center zone from which the radially extending zones extend. In one embodiment, the center zone is substantially round, such as circular or oval. A majority of the center zone of the wafer may be inside the bag when such is attached. The attachment line of the bag may be inside the center zone. The attachment line may be concentrically to the center zone. The center zone is at least 10 mm broader (measured in radial direction) than the attachment line in order to ensure good attachment of the wafer and leakage control.

The adhesive wafer may comprise a plurality of radially extending zones, such as three, four, five, six, seven, eight etc. The radially extending zones may be spaced a part equidistantly around the circumference of the center zone.

In one embodiment, the first zone is shaped like a flower where the radially extending zones correspond to the leaves of the flower. In one embodiment, each of the radially extending zones terminates in a point with a predetermined radius. In one embodiment, the width of each radially extending zone decreases in the direction of the point towards which the radially extending zone terminates.

In one embodiment, the radially extending zone comprises a part along which the width is constant. The width of the radially extending zone being measured in a direction transverse to the longitudinal direction of the radially extending zone. In one embodiment, one or more of the radially extending zones comprises a part where the width increases in the direction of a tip of the radially extending zone.

In one embodiment, the interconnecting parts extend in a radial direction. In other embodiments, the interconnecting parts are provided in the form of bands which interconnect the radially extending zones. Any two neighboring radially extending zones may be interconnected by one or more of such bands, each of which extend in a direction transverse to the longitudinal direction of the radially extending zones. Accordingly, in one embodiment, the adhesive wafer is shaped like a spider web.

In one embodiment, the second zone encirculates the first zone. In the latter embodiment, each of the interconnecting parts may extend (radially inwards) towards the center of the first zone, e.g. such that they fill out the space defined between the radially extending zones. Moreover, the outer shape of the second zone may be round such as oval or circular. In the latter embodiment, the second zone defines the outer rim of the adhesive wafer.

In embodiments where the second zone does not encirculate the first zone, a part of the outer rim of the adhesive wafer may be defined by the first zone, while another part of the adhesive wafer is defined by the second zone.

A part of the second zone defines at least 30% of the total circumference of the outer rim of the adhesive wafer. The part of the second zone may for example constitute at least 30%, such as at least 40%, such as at least 50%, such as at least 60%, such as at least 70%, such as at least 80%, such as at least 90%, such as 100% of the of the total circumference of the outer rim of the adhesive wafer.

The area of the second zone may for example comprise 10-80%, such as 20-70%, such as 30-70%, such as 30-60% of the total area of the wafer.

In one embodiment, the second zone defines one unitary zone while the second zone in other embodiments defines a plurality of non-unitary zones. The latter non-unitary zones may be interconnected via the first zone.

In one embodiment, an interconnecting part is defined between any two neighboring radially extending zones. In another embodiment, the each radially extending part is only connected to one other radially extending part by means of an interconnecting part.

The wafer has in a first zone a first set of properties and in a second zone a second set of properties. The properties of the first and the second zone may be achieved by the properties of the adhesive layer, the backing layer or a combination of both.

The skin-facing surface of both the first and the second zone is adhesive.

In one embodiment the backing layer in a first zone has a first set of properties and in a second zone has a second set of properties.

As an example, the yield strength of the first zone and the yield strength of the second zone are identical. In the context of the present invention the term 'yield strength' or 'yield point' shall be understood as the level of stress a material must be subjected to before starting to deform plastically. Prior to the yield point, the material will deform elastically, and will return to its original shape, when the applied stress is removed. Once the yield point is passed, some fraction of the deformation will be permanent and non-reversible. By providing identical yield strengths of the first and the second zone, it may be ensured that none of the first zone and the second zones are more prone to deforming plastically than the other.

In another embodiment, the yield strength of the second zone is higher than the yield strength of the first zone. The effect is that for the second zone—which defines the interconnecting parts—may be deformed elastically in a larger stress range than the first zone. In effect the second zone is more elastic than the first zone.

In yet another embodiment, the yield strength of the second zone is lower than the yield strength of the first zone. The effect is that the second zone—which defines the interconnecting parts—may easily be stretched relative to the first zone which defines the radially extending zones. This provides the user with the advantage that it is easier to adapt the geometry of the adhesive wafer to the geometry of the user—which is especially advantageous for example in cases where a hernia is associated with the stoma.

Another example of different properties of the first and the second zone is the stiffness. Accordingly, the stiffness of the first zone may be larger than the stiffness of the second zone. One advantage of providing stiffer first zones is that the radially extending zones will be stiffer than the interconnecting parts. This may make it easier to remove the adhesive wafer from the skin of the user as the user may disengage the adhesive wafer from the skin by peeling off the relatively stiff radially extending parts. As these radially extending parts are interconnected by means of the interconnecting parts, the adhesive wafer may be removed in one single motion. When the second zones are less stiff than the radially extending zones, it may be easier for the user to fasten the adhesive wafer to the skin of the user. This is especially the case when the second zones are more flexible than the radially extending zones. Moreover, an adhesive wafer with stiff zones and less stiff zones may be more comfortable to wear as the less stiff zones may allow the stiffer zones to move easily relative to each other e.g. when the user bends the stomach.

One way of making the second zone stiffer than the first zone is by providing the two zones in different thicknesses. Accordingly, in one embodiment, the second zone is thicker than the first zone in a direction transverse to line extending radially from the passage of the adhesive wafer.

The first and the second zones may comprise different adhesives, for example a soft adhesive and a stiffer adhesive or adhesives with different absorption properties. The different adhesive may be combined with different thicknesses in order to enhance the difference in properties.

The first zone may have an adhesive tack being higher than the adhesive tack of the second zone.

The adhesive of the first zone may be an adhesive being suitable to have close to the stoma, for example an absorbent adhesive or an erosion resistant adhesive.

The second zone may be very thin and flexible. When applying the wafer to a protruding surface such as a hernia or an inward stoma the radially extending zones may be applied without wrinkles and any surplus of the wafer in the interconnecting second zone may be crinkled, crumbled to fit. If the second zone is thin and flexible, any folds and crinkles will be very small and flat and does not give rise to leakages or friction, but on the contrary provide a snug fit to the skin.

The thickness of the second zone may be smaller than the thickness of the first zone. The second zone may have a thickness being less than 70%, such as less than 60%, such as less than 50, such as less than 40%, such as less than 30%, such as less than 20% or such as less than 10% of the thickness of the first zone.

The thickness of the second zone may be 50-1500 µm, such as 50-1000 µm, such as 50-750 µm. The thickness of the second zone may vary, such that for example the interconnecting part may be thicker than the outer ring part or the outer ring part may be thicker than the interconnecting parts.

The thickness of the first zone may be 500-3000 µm, such as 1000-3000 µm. The thickness of the first zone may vary, such that for example the radially extending zones may be thicker than the center zone or the center zone may be thicker than the radially extending zones. The thickness of the radially extending zones may increase or decrease radially.

The thickness of the wafer is measured in a direction perpendicular to the skin-facing surface of the wafer.

The backing layer may be elastic in order to better be able to adapt to the contours of the skin.

The edge portion of the wafer may be beveled in order to provide a smooth transition to the skin and avoid rolling up of the edges. The first zone may be beveled at the edge portions in the case where the first zone is thicker than the second zone.

In one embodiment, the absorption capacity of the first and the second zone are identical. Alternatively, an absorption capability of the second zone is higher than an absorption capability of the first zone or the absorption capability of the first zone may be higher than the absorption capability of the second zone.

BRIEF DESCRIPTION OF THE FIGURES

The invention will now be described with reference to the figures in which.

DETAILED DESCRIPTION OF THE FIGURES

Figure 1:
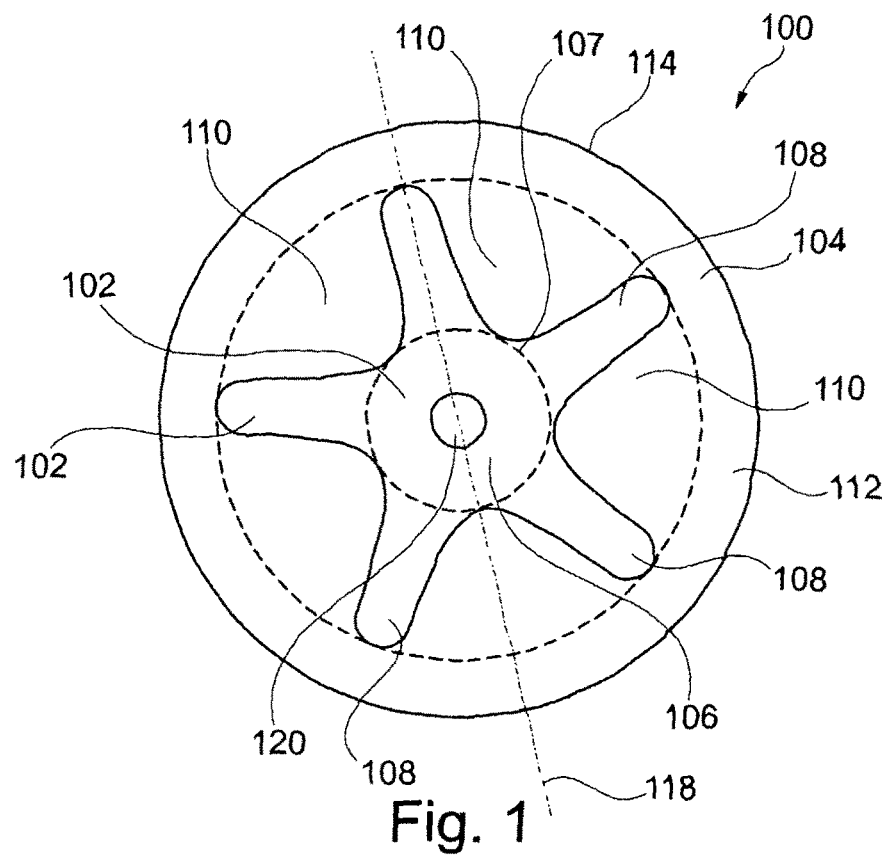
FIG. 1 discloses a first embodiment of the adhesive wafer.

FIG. 1 discloses an adhesive wafer 100 comprising a first zone 102 and a second zone 104. Each first zone 102 defines a centre zone 106 which is indicated by dotted line 107 and one or more radially extending zones 108. In the embodiment of FIG. 1 five radially extending zones 108 are provided. The second zone 104 defines one or more interconnecting parts 110 each of which interconnects at least two of the radially extending zones. In the embodiment of FIG. 1 the interconnecting parts 110 fill the space defined between the radially extending zones 108. Moreover, the second zone 104 defines an outer ring part 112, which encirculates the first zone 102 and the interconnecting parts 110. It will be appreciated that in some embodiments, the outer ring part 112 is not provided whereby the outer rim 114 of adhesive wafer 100 is defined by the tip of the radially extending zones 108 and the outermost part of the interconnecting parts 110.

Figure 2:
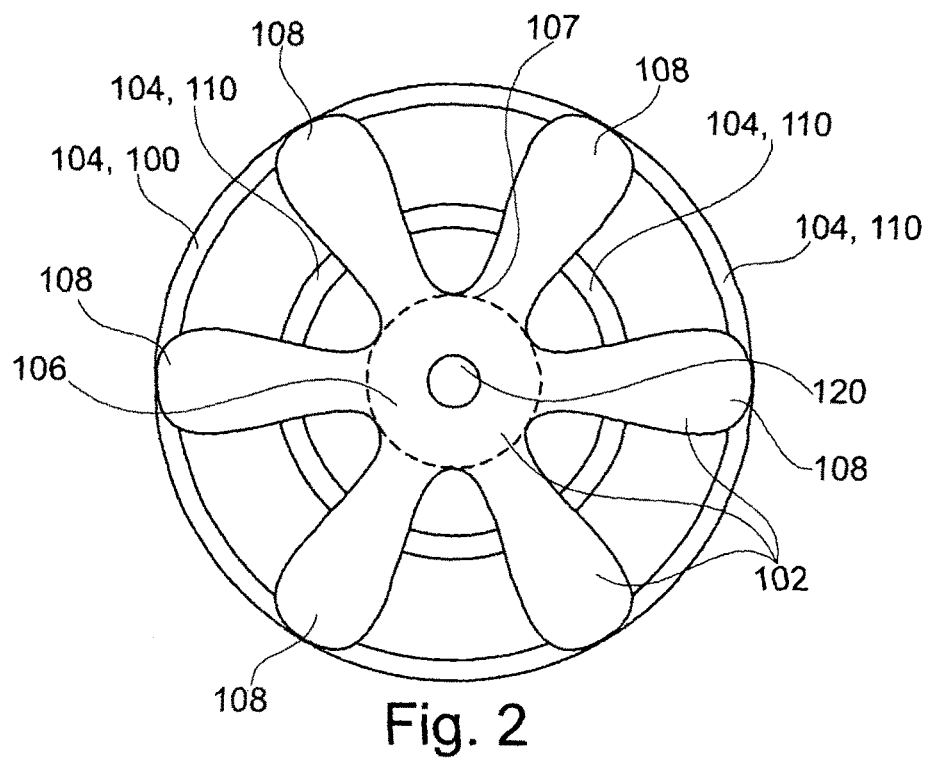
FIG. 2 discloses a second embodiment of the adhesive wafer.

In FIG. 2, the first zone 102 comprises six radially extending zones 108. Each of these zones 108 are interconnected by circumferentially extending interconnecting parts 110, which thus define the second zone 104.

In both embodiments (FIGS. 1 and 2) it will be appreciated that once the user peels off one of the radially extending zones 108 the interconnecting parts 110 will cause the remaining radially extending zones 108 to be peeled off, as initially the two neighbouring radially extending zones 108 are peeled off and subsequently the next neighbouring radially extending zones 108.

It will be appreciated that due to the design the centre zone 106 and the radially extending zones 108 may be made relatively thick having a high absorption capacity, e.g. with materials such as hydrocolloids. As not the entire adhesive wafer 100 is made from such a thick layer, the adhesive wafer 100 is more comfortable for the user to wear. The purpose of the interconnecting parts 110 may be to cause the remaining radially extending zones 108 to be peeled off when one of these zones 108 is peeled off.

Figure 3:
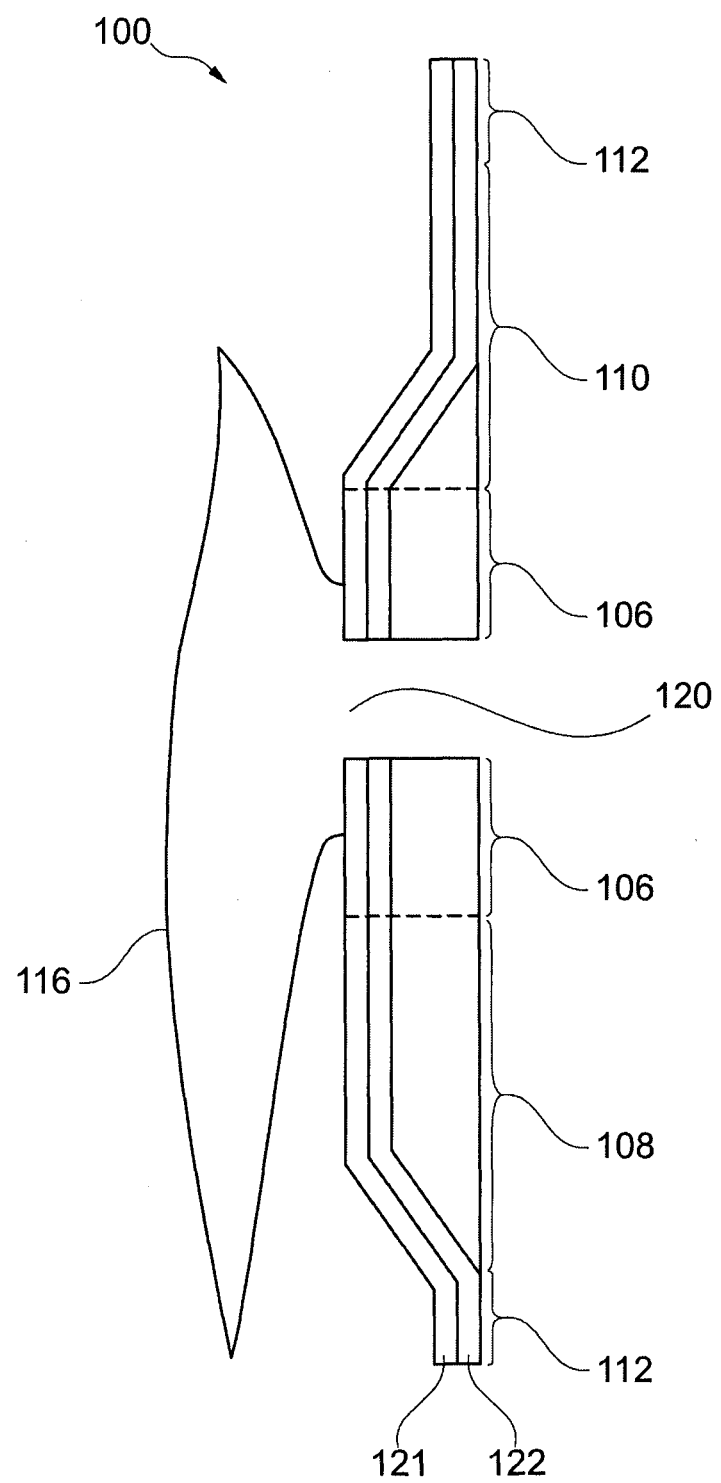
FIG. 3 discloses an ostomy appliance according to the present invention.

FIG. 3 discloses a cross-sectional view of the adhesive wafer 100 comprising a collecting bag 116 the section through the adhesive wafer 100 corresponds to that of line 118 in FIG. 1. Accordingly, it will be appreciated in FIG. 3 that in the upper part of the adhesive wafer 100, only the centre zone 106, the interconnecting parts 110 and the outer ring part 112 is visible, while in the lower part of the adhesive wafer 100 the centre zone 106, the radially extending zone 108 and the outer ring part 112 is visible. Naturally, the aperture 120 is also visible in the figure.

In the embodiment of FIG. 3, the collecting bag 116 is secured to the adhesive wafer 100. However in other embodiments, the collecting bag 116 may be fastened to the adhesive wafer 100 by the user, whereby the adhesive wafer 100 may be reused for the next collecting bag 116.

In the embodiment of FIG. 3, the first zone 106, 108 is in the form of a layer of adhesive being beveled at the edge portion. The second zone comprises a thin layer of adhesive 122 coated on a backing layer 121. In this embodiment the entire backing layer 121, including the part covering the first zone 106, 108, is provided with adhesive 122.

The invention claimed is:

1. An ostomy appliance attachable around a stoma, the ostomy appliance comprising:
   an adhesive wafer defining a passage for receiving the stoma, the adhesive wafer comprising:
      a backing layer having a proximal side and an opposite distal side and a skin facing adhesive deposited on the proximal side of the backing layer, with the backing layer extending from an edge of the passage to an outer peripheral edge of an outer perimeter of the adhesive wafer, and the skin facing adhesive deposited on the backing layer from the edge of the passage to the outer peripheral edge of the outer perimeter of the adhesive wafer;
      a collecting bag attachable to the distal side of the backing layer of the adhesive wafer;
      wherein the skin facing adhesive comprises:
         a first adhesive zone and
         a separate second adhesive zone,
         wherein the first adhesive zone comprises a central adhesive zone that surrounds the passage and three or more radial adhesive zones that are connected to and extend radially from the central adhesive zone towards the outer peripheral edge of the adhesive wafer,
   wherein the second adhesive zone comprises two or more interconnecting parts that are separated from each other and each separately interconnects each of the three or more radial adhesive zones to another of the three or more radial adhesive zones,
   wherein each of the interconnecting parts of the second adhesive zone extends in an arc around the passage; and
   wherein at least one of the interconnecting parts of the second adhesive zone is provided as part of the skin facing adhesive provided in the outer perimeter of the adhesive wafer.

2. The ostomy appliance according to claim 1, wherein the interconnecting part is defined between any two neighboring radially extending zones.

3. The ostomy appliance according to claim 1, wherein a yield strength of the first adhesive zone and a yield strength of the second adhesive zone are identical.

4. The ostomy appliance according to claim 1, wherein a yield strength of the first adhesive zone is higher than a yield strength of the second adhesive zone.

5. The ostomy appliance according to claim 1, wherein a stiffness of the first adhesive zone is larger than a stiffness of the second adhesive zone.

6. The ostomy appliance according to claim 1, wherein the second adhesive zone is thicker than the first adhesive zone in a direction transverse to a line extending radially from the stoma passage of the adhesive wafer.

7. The ostomy appliance according to claim 1, wherein the first adhesive zone is thicker than the second adhesive zone in a direction transverse to a line extending radially from the stoma passage of the adhesive wafer.

8. The ostomy appliance according to claim 1, wherein an absorption capability of the first adhesive zone is higher than an absorption capability of the second adhesive zone.

9. The ostomy appliance according to claim 1, wherein a shape of the adhesive wafer is circular or oval.

10. The ostomy appliance according to claim 1, wherein the three or more radial adhesive zones are spaced apart equidistantly around a circumference of the central adhesive zone.

11. The ostomy appliance according to claim 1, wherein the central adhesive zone is circular or oval.

12. The ostomy appliance according to claim 1, wherein each of the three or more radial adhesive zones terminates in a point located at a predetermined radial distance from a center of the passage.

13. The ostomy appliance according to claim 1, wherein the interconnecting part extends radially from the passage.

14. The ostomy appliance according to claim 1, wherein the interconnecting part is an annular band.

15. The ostomy appliance according to claim 1, wherein the first and second adhesive zones combine to define a spider web configuration of the adhesive wafer.

16. The ostomy appliance according to claim 1, wherein the second adhesive zone is located at the outer peripheral edge of the outer perimeter.

17. The ostomy appliance according to claim 1, wherein the second adhesive zone extends a distance of at least 30% of a circumference of the outer perimeter of the adhesive wafer.

18. The ostomy appliance according to claim 1, wherein each of the three or more radial adhesive zones has a first width measured at the central adhesive zone and a second width measured at the second adhesive zone, with the first width larger than the second width.

19. The ostomy appliance according to claim 1, wherein the outer perimeter of the adhesive wafer, including both a backing layer outer perimeter and a second adhesive zone outer perimeter, extends radially outward from outer edges of the three or more radial adhesive zones.

20. The ostomy appliance according to claim 1, wherein at least one of the interconnecting parts of the second adhesive zone is provided as part of adhesive zone outer perimeter of the outer perimeter of the skin facing surface of the second adhesive zone; and
   a skin facing surface of the adhesive zone outer perimeter of the outer perimeter is configured to attach to skin around the stoma.

21. The ostomy appliance according to claim 1, wherein the adhesive wafer includes a collecting bag adhesive that is deposited on the distal side of the backing layer, and further wherein the collecting bag adhesive is in a pattern different from the first adhesive zone and the separate second adhesive zone of the skin facing adhesive.

22. The ostomy appliance according to claim 1, wherein the collecting bag includes a collecting bag adhesive that is deposited on a portion of the collecting bag, and further wherein the collecting bag adhesive is in a pattern different from the first adhesive zone and the separate second adhesive zone of the skin facing adhesive.

23. An adhesive wafer defining a passage for receiving a stoma, the adhesive wafer comprising:
a backing layer having a proximal side and an opposite distal side;
a skin facing adhesive deposited on the proximal side of the backing layer, with the backing layer extending from an edge of the passage to an outer peripheral edge of an outer perimeter of the adhesive wafer, with the skin facing adhesive deposited on the backing layer from the edge of the passage to the outer peripheral edge of the outer perimeter of the adhesive wafer;
wherein the skin facing adhesive comprises:
a first adhesive zone and
a separate second adhesive zone,
wherein the first adhesive zone comprises a central adhesive zone that surrounds the passage and three or more radial adhesive zones that are connected to and extend radially from the central adhesive zone towards the outer peripheral edge of the adhesive wafer,
wherein the second adhesive zone comprises two or more interconnecting parts that are separated from each other and each separately interconnects each of the three or more radial adhesive zones to another of the three or more radial adhesive zones,
wherein each of the interconnecting parts of the second adhesive zone extends in an arc around the passage, and
wherein at least one of the interconnecting parts of the second adhesive zone is provided as part of the skin facing adhesive provided in the outer perimeter of the adhesive wafer.

\* \* \* \* \*